United States Patent [19]

Inoue

[11] Patent Number: 5,230,889
[45] Date of Patent: Jul. 27, 1993

[54] ENRICHED NUTRITIOUS FOOD PRODUCT COMPRISING POWDER OF GINSENG AND METHOD FOR PRODUCING POWDER OF GINSENG

[75] Inventor: Mitsuyori Inoue, Tokyo, Japan

[73] Assignee: Iwatani Sangyo Kabushiki Kaisha, Japan

[21] Appl. No.: 836,708

[22] Filed: Feb. 19, 1992

[30] Foreign Application Priority Data
Apr. 12, 1991 [JP] Japan .................................. 3-108528

[51] Int. Cl.$^5$ ........................ A61K 35/78; A23C 1/06
[52] U.S. Cl. .................................. 424/195.1; 426/384
[58] Field of Search ...................... 424/195.1; 426/384

[56] References Cited

U.S. PATENT DOCUMENTS 4,426,398  1/1984  Kokura et al. ........................ 426/72

OTHER PUBLICATIONS

H. Park et al. Chem Abst. 114 (21):205701y, 1991.

Primary Examiner—John W. Rollins
Attorney, Agent, or Firm—Bacon & Thomas

[57] ABSTRACT

A ginseng powder is produced as follows. Firstly, a ginseng harvested from a field is washed within at least 24 hrs. after harvest in the raw state. Then, the washed ginseng is dried under such a condition that it is not subjected to temperatures above 40° C. After that, the dried ginseng is put in liquid nitrogen so as to have a low temperature brittleness. Subsequently the whole of the ginseng is crushed into powder at a time within a nitrogen gas atmosphere at an evaporation temperature of the liquid nitrogen.

12 Claims, 2 Drawing Sheets

ENRICHED NUTRITIOUS FOOD PRODUCT COMPRISING POWDER OF GINSENG AND METHOD FOR PRODUCING POWDER OF GINSENG

BACKGROUND OF THE INVENTION

The present invention relates to an enriched nutritious food product comprising a powder of ginseng used as raw materials for a herb medicine and a method for producing the powder of ginseng. More specifically, besides *Panax schinseng*, such ginseng includes *Panax japonicus*, *Panax quinquefolium* and *Acanthopanax senticosus* containing medicinal effective ingredients similar thereto.

For example, the ginseng to be used for the herb medicine and the enriched nutritious food product is a perennial plant of Alaliacea family having the botanical name of *Panax schinseng*, which is distributed over a region from the northeastern district of China to Korea and cultivated also in Japan, namely in Shimane prefecture and so on.

The botanical name of "Panax" means the complete healing, namely a cure-all and originates in the PAN (all) and the AKOS (healing) of Greek. This ginseng is effective as the herb medicine for additionally filling up spirits of the main entrails of the liver, the heart, the spleen, the lugs and the kidney.

As substitutes for this ginseng there has been provided *Panax japonicaus*, *Panax quinquefolium* or *Acanthopanax senticosus* of similar kind having the same medicinal effects.

A main ingredient of the ginseng is saponin. As the saponin included in this ginseng there have been known twelve kinds of ginsenside-Ro, -Ra, -Rb1, -Rb2, -Rc, -Rd, -Re, -Rf, -Rg1, -Rg2, -Rg3, -Rh. These are the one (ginsenside-Rb1, -Rb2, -Rc) containing sapogenen and protopanaxadiol, and the one (ginsenside-Re, Rf, -Rg1, -Rg2) containing sapogenen and protopanaxatriol. The main saponin in the crude drug is ginsenside-Rb1, -Rb2, -Rc, -Rg1. The ginsenside-Ro is the same as chikusetsusaponin V, and the ginsenside-Rb1 is the same as saponin D.

Besides those, the ginseng contains essential oil of 0.05%, $\beta$-elemene, panacene ($C_{15}H_{24}$) and panaxynol as polyacetylene compound and further contains choline, vitamin B complex, fatty acid and so on.

Since owing to the above-mentioned ingredients the ginseng provides both sedation for body and mind disease and the likes and normalizing effect for metabolism, it is typical of robustness type enriched nutritious food products and herb medicines.

In that way, the ginseng has been highly esteemed as valuable drugs since ancient times and there were conventionally following two methods for preparing raw materials to be used for enriched nutritious food products and herb medicines.

According to the first method, raw ginsengs harvested from fields are washed and then dried by the sun or heating as they are or after having been put through the hot water. According to the second method, raw ginsengs are washed, steamed at temperatures below 130° C. and then dried by heating at 70° C.

Both those preparation methods are used in Japanese markets, and ginseng drugs containing sufficient amount of the above-mentioned ingredients are judged good in quality even though they are prepared in either method.

Then, the ginseng extract is obtained from those prepared raw ginsengs by means of alcohol- or water-extracting method. The ginseng extract is used as it is or in granular state for enriched nutritious food products and herb medicines such as various kinds of drink drugs, tablet drugs or teas.

However, according to either conventional method for preparing such raw material, since the ginseng is to be heated at temperatures above 40° C. at the time of heating or drying, disadvantageously a portion of the saponin of the main ingredient is destroyed.

Further, since the ginseng extract is obtained by extracting only the saponin group, part of the ingredient obtained from the partially destroyed prepared raw material, the extract is lack of useful ingredients inherent to ginseng. Especially other effective ingredients except the saponin ingredients are not utilized effectively at all so far.

That is, conventional, so-called ginseng products have come off largely from the effective ingredients of the raw ginseng harvested from fields.

Accordingly, in view of the above-mentioned problems desired is a high-quality ginseng raw material suitable for various applications to present enriched nutritious food products and herb medicines.

SUMMARY OF THE INVENTION

The present invention is directed to solving the above-mentioned problems and has for its objects to provide enriched nutritious food products which can be used as raw materials for nutritious foods and herb medicines and comprise high-quality ginseng powders having various kinds of useful original ingredients and also to provide the method for producing such ginseng powder.

For accomplishing the aforementioned objects, the present invention comprises as follows. That is, ginsengs harvested from fields are washed at least within 24 hrs. after harvest in a raw state. Then, the ginsengs are dried under such a condition that they are not heated at temperatures above 40° C. After that, they are put in liquid nitrogen to have a low temperature brittleness. Thereupon, the whole of the ginsengs are crushed into powder at a time within an atmosphere at a liquid nitrogen temperature to produce the powder of ginseng.

In another method for producing the ginseng powder, the ginsengs are washed, subjected to the above-mentioned crushing process employing the liquid nitrogen and then dried under such a condition that they are not heated at temperatures above 40° C.

The ginseng powder obtained in that way can be used for production of enriched nutritious food products by mixing it with other herb medicines and/or foods.

Since the ginseng powder obtained in accordance with the producing method of the present invention is not subjected to the temperatures above 40° C. during the drying process, the effective ingredients such as saponin and the like contained in the ginseng are not destroyed. Further, since the ginseng is crushed into powder within the atmosphere at the liquid nitrogen temperature, it is never subjected to an oxidization by heat and air.

Further, since the whole of the ginseng is crushed into powder, the obtained powder contains all of the effective ingredients of the ginseng to have extremely high-quality.

Since the ginseng products obtained in accordance with the producing method of the present invention are in the dry powder state, they can be handled as a simple substance product, readily circulated and processed. For example, the powder can be usually readily taken as a medicine in a capsule or an enriched nutritious food product. Further, the powder can be used as a raw material suitable for various applications to enriched nutritious food products, herb medicines and so on by mixing it with other herb medicines and/or foods to produce new nutritious staminal drugs, so that the ginseng can be utilized effectively maximally.

Further, according to the present invention, when the ginseng cultivated without any agricultural chemicals is used as ginseng for a raw material, any residuals of agricultural chemicals are not contained in the foods, so that the foods comprising extremely safe ginseng powder can be provided.

BRIEF DESCRIPTION OF THE DRAWINGS

FIG. 1 is a block diagram of a production process;

FIG. 2 is a schematic view of an apparatus to be used for freezing and crushing process.

DETAILED DESCRIPTION OF PREFERRED EMBODIMENTS

First Embodiment

Figure 1:
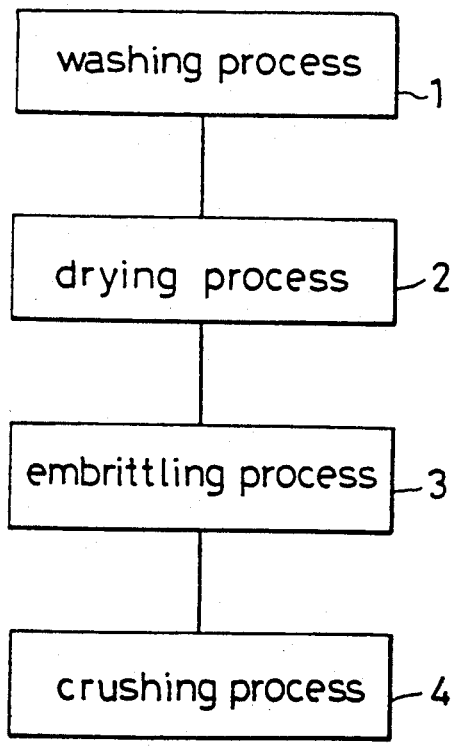
FIGS. 1 and 2 show a first embodiment of the present invention.
Figure 2:
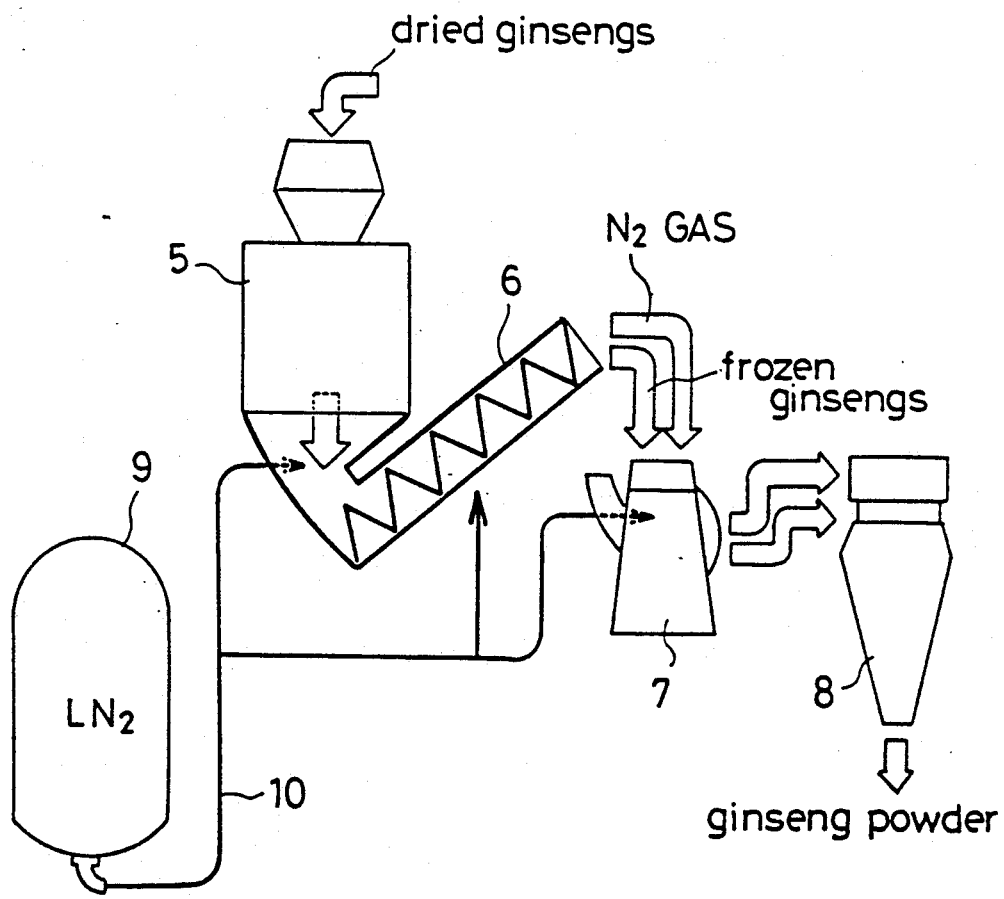

FIGS. 1 and 2 show a first embodiment of the present invention.

As shown in FIG. 1, in this embodiment, a powder of ginseng (referred to as a ginseng powder hereinafter) is produced by means of a washing process 1, a drying process 2, an embrittling process 3 and a crushing process 4 in order.

Before the washing process 1, ginsengs (*Panax schinsengs*) having roots of six years old are harvested from fields for use as a ginseng raw material. During the washing process 1, the harvested ginsengs are washed at least within 24 hrs., preferably just after harvest so as to remove foreign substances completely therefrom.

Incidentally, it is not necessary to limit the ginseng used for the raw material to such a one as having the root of six years old and roots of any years old may be used, but it is preferable to use ginsengs having roots of 4~7 years old from viewpoint of effective ingredients contained therein.

Preferably by using such ginsengs that are cultivated without any agricultural chemicals, namely by means of so-called organic agricultural method, there is nothing to worry about residuals of agricultural chemicals in the ginsengs so as to provide safe products. But, besides it is also possible to use for the raw material such ginsengs that are cultivated by using agricultural chemicals harmless for human health.

Next, during the drying process 2, the washed ginseng is dried by means of freeze-dry method under such a condition that the ginseng is not subjected to temperatures above 40° C. so that its moisture content becomes at most 4%.

For other drying methods besides the freeze-dry method, for example far-infrared radiation and microwave radiation may be used optionally so that the ginseng is not subjected to the temperatures above 40° C.

After a brittleness has been added by embrittling process 3 to the dried ginsengs by means of an apparatus shown in FIG. 2, they are crushed into powder during the crushing process 4.

In FIG. 2, the symbol 5 designates a freezing hopper. A screw-type feeder 6 is disposed in a lower portion of the freezing hopper 5 so as to be communicated therewith, and a crusher 7 is disposed on a downstream side of the screw-type feeder 6 so as to be communicated with a cyclone-type collector 8 through a passage.

Thereupon, a liquid nitrogen at 77 K. (−196° C.) is supplied to each interior of the freezing hopper 5, the screw-type feeder 6 and the crusher 7 respectively from a separate liquid nitrogen tank 9 through a piping 10, and all interiors thereof are set to an ultracold atmosphere.

During the embrittling process 3, firstly the dried ginsengs are supplied into the freezing hopper 5. Since the liquid nitrogen at 77 K. supplied from the liquid nitrogen tank 9 is contained within the freezing hopper 5, the supplied ginsengs are put in the liquid nitrogen so as to be frozen instantly to have a brittleness.

Subsequently the ginsengs having the brittleness provided by the instant freezing are fed to the crusher 7 by means of the screw-type feeder 6 so as to be crushed during the crushing process 4. A nitrogen gas atmosphere at 77 K. is provided within the crusher 7 by the liquid nitrogen supplied from the liquid nitrogen tank 9. The frozen ginsengs fed by the screw-type feeder 6 are finely crushed into powder whose particle size is at most 100 mesh, preferably at most 200 mesh within the ultracold nitrogen gas atmosphere. When the ginsengs are crushed into powder of fine particle size in that way, it becomes easier to mix them with other herb medicines and foods.

Thereupon, since the ginsengs are crushed into powder within the nitrogen gas atmosphere at the evaporation temperature of the liquid nitrogen at 77 K., the ginsengs are not subjected to the oxidization by heat and air at all so that all special medicinal ingredients of the ginseng can be preserved in the finely crushed powder.

The powder of the ginsengs crushed finely by means of the crusher 7 is taken out after being collected by means of the cyclone-type collector 8.

By operating the above-mentioned apparatus, the finely crushed powder of the ginseng of 98 kg can be obtained from the dried ginsengs of 100 kg supplied into the freezing hopper 5.

The ginseng powder produced in accordance with the above-mentioned procedures is mixed with other herb medicines and foods to produce enriched nutritious food products and herb medicines having such forms as various drink drugs, tablets, teas and so on.

Such ginseng powder is fine in particle size and is readily handled for circulation and preservation. Further, the ratio of mixing with foods can be precisely managed and ginseng powder also can be handled readily to be mixed therewith. Furthermore, since all medicinal ingredients of the ginseng are almost never destroyed but preserved in the ginseng powder, the food products comprising such ginseng powder can be made high-quality enriched nutritious food products.

In the above-mentioned embodiment, though *Panax schinseng* has been used as one example ginseng, besides it other similar ginsengs such as *Panax japonicus, Panax*

*quinquefolium* or *Acanthopanax senticosus* having the same ingredients as those of the *Panax schinseng* may be used. (Second Embodiment)

Figure 3:
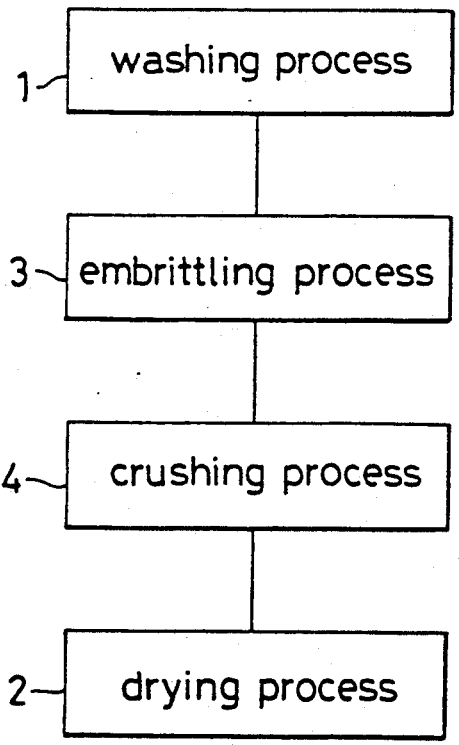
FIG. 3 shows a second embodiment of the present invention and is a view corresponding to FIG. 1.

FIG. 3 shows a second embodiment. In this embodiment, there are provided the embrittling process 3 and the crushing process 4 after the washing process 1, and the drying process 2 is arranged after that. The ginsengs are processed during the respective processes similarly to the respective processes of the first embodiment.

As many different embodiments of the invention will be obvious to those skilled in the art, some of which have been disclosed or referred to herein, it is to be understood that the specific embodiments of the present invention as presented herein are intended to be by way of illustration only and are not limiting on the invention, and it is to be understood that such embodiments, changes, or modifications may be made without departing from the spirit and scope of the invention as set forth in the claims appended hereto.

What is claimed is:

1. A method for producing ginseng powder comprising the steps of:
   (a) washing a ginseng harvested from a field, within at least 24 hours after harvest in the raw state;
   (b) drying the ginseng under such a condition that it is not subjected to temperature above 40° C. so as to make the moisture content of the ginseng at most 4%;
   (c) putting the ginseng in liquid nitrogen so as to freeze it and to give a low temperature brittleness to it; and
   (d) crushing the whole of the ginseng at a time within a nitrogen gas atmosphere at an evaporation temperature of the liquid nitrogen under its frozen embrittled condition.

2. A method for producing ginseng powder as set forth in claim 1, wherein said ginseng harvested from the field is such a one cultivated without use of any agricultural chemicals.

3. A method for producing ginseng powder as set forth in claim 1, wherein the ginseng powder is made less than 200 mesh in particle size by said crushing step.

4. A method for producing ginseng powder comprising the steps of:
   (a) washing a ginseng harvested from a field, within at least 24 hours after harvest in the raw state;
   (b) putting the ginseng in liquid nitrogen so as to freeze it and to give a low temperature brittleness to it;
   (c) crushing the whole of the ginseng at a time within a nitrogen gas atmosphere at an evaporation temperature of the liquid nitrogen under its frozen embrittled condition; and
   (d) drying the ginseng under such a condition that it is not subjected to temperatures above 40° C. so as to make the moisture content of the ginseng at most 4%.

5. A method for producing ginseng powder as set forth in claim 4, wherein said ginseng harvested from the field is such a one cultivated without use of any agricultural chemicals.

6. A method for producing ginseng powder as set forth in claim 4, wherein the ginseng powder is made less than 200 mesh in particle size by said crushing step.

7. An enriched nutritious food product comprising ginseng powder made by:
   (a) washing a ginseng harvested from a field, within at least 24 hours after harvest in the raw state;
   (b) drying the ginseng under such a condition that it is not subjected to temperatures above 40° C. so as to make the moisture content of the ginseng at most 4%.
   (c) putting the ginseng in liquid nitrogen so as to freeze it and to give a low temperature brittleness to it; and
   (d) crushing the whole of the ginseng at a time within a nitrogen gas atmosphere at an evaporation temperature of the liquid nitrogen under its frozen embrittled condition.

8. An enriched nutritious food product comprising ginseng powder as set forth in claim 7, wherein said ginseng harvested from the field is such a one cultivated without use of any agricultural chemicals.

9. An enriched nutritious food product comprising ginseng powder as set forth in claim 7, wherein the ginseng powder is made less than 200 mesh in particle size by said crushing step.

10. An enriched nutritious food product comprising ginseng powder made by:
    (a) washing a ginseng harvested from a field, within at least 24 hours after harvest in the raw state;
    (b) putting the ginseng in liquid nitrogen so as to freeze it and to give a low temperature brittleness to it;
    (c) crusing the whole of the ginseng at a time within a nitrogen gas atmosphere at an evaporation temperature of the liquid nitrogen under its frozen embrittled condition; and
    (d) drying the ginseng under such a condition that it is not subjected to temperatures above 40° C. so as to make the moisture content of the ginseng at most 4%.

11. An enriched nutritious food product comprising ginseng powder as set forth in claim 10, wherein said ginseng harvested from the field is such a one cultivated without use of any agricultural chemicals.

12. An enriched nutritious food product comprising ginseng powder as set forth in claim 10, wherein the ginseng powder is made less than 200 mesh in particle size by said crushing step.

* * * * *